United States Patent
Löll

[19]

[11] Patent Number: 6,072,575
[45] Date of Patent: Jun. 6, 2000

[54] DEVICE FOR INSPECTING BOTTLES AND THE LIKE

[75] Inventor: Josel Löll, Regenburg, Germany

[73] Assignee: Krones AG, Neutraubling, Germany

[21] Appl. No.: 09/091,972

[22] PCT Filed: Oct. 30, 1997

[86] PCT No.: PCT/EP97/05992

§ 371 Date: Jan. 25, 1999

§ 102(e) Date: Jan. 25, 1999

[87] PCT Pub. No.: WO98/19150

PCT Pub. Date: May 7, 1998

[30] Foreign Application Priority Data

Oct. 30, 1996 [DE] Germany ............ 296 18 394 U
Sep. 19, 1997 [DE] Germany ............ 297 16 878 U

[51] Int. Cl.[7] .................................................. G01N 21/00
[52] U.S. Cl. ........................... 356/239.4; 356/239.1; 356/239.2; 356/239.5; 356/239.6
[58] Field of Search .................... 356/239.1, 239.2, 356/239.4, 239.5, 239.7, 240.1

[56] References Cited

U.S. PATENT DOCUMENTS

| | | |
|---|---|---|
| 4,025,201 | 5/1977 | Deane . |
| 4,249,075 | 2/1981 | Lovalenti ............... 356/240 |
| 4,750,035 | 6/1988 | Chang et al. . |
| 4,914,289 | 4/1990 | Nguyen et al. ............ 356/240 |
| 5,536,935 | 7/1996 | Klotzsch et al. ............ 356/240 |

FOREIGN PATENT DOCUMENTS

| | | |
|---|---|---|
| 0 512 539B1 | 7/1992 | European Pat. Off. . |
| 0 657 732A1 | 10/1994 | European Pat. Off. . |
| 9313115 | 11/1994 | Germany . |
| 29502708 U1 | 5/1996 | Germany . |
| 2288016 | 10/1995 | United Kingdom . |
| WO 91/08468 | 6/1991 | WIPO . |

OTHER PUBLICATIONS

Abstract of Japanese Publlication No. 04297810 of Mitsubishi Materials Corp.
International Search Report (PCT Forms 220 and 210).

*Primary Examiner*—Frank G. Font
*Assistant Examiner*—Roy M. Punnoose
*Attorney, Agent, or Firm*—Tilton, Fallon, Lungmus & Chestnut

[57] ABSTRACT

To record an image of the mouth area (2) of a bottle (1), a luminous surface (3) is arranged below the mouth area to be recorded. The luminous surface (3) is lighted by means of a lighting device (4) and the image of the lighted mouth area (2) is sent to a camera by a mirror arrangement (5, 6, 11). With the luminous surface, it is possible to image the mouth area in transmitted light, which yields improved detection of defects and soiling in the mouth area and thus permits easier evaluation of the image recorded by the camera.

43 Claims, 9 Drawing Sheets

6,072,575

DEVICE FOR INSPECTING BOTTLES AND THE LIKE

FIELD AND BACKGROUND OF THE INVENTION

This invention relates to a device for inspecting bottles or the like, with a light source, an image recording element with a respective image analyzing device and a one-piece optical body made of a transparent material. Such a device is known from Unexamined European Patent No. 657,732. The device shown in various modifications in FIGS. 11 through 14 of this document has a ring-shaped optical body with an input and output surface for the optical beam paths. The internal and external ring surfaces of the body are mirrorized, so that an optical beam coming from the bottle is deflected in the direction of the image recording element by reflection after entering the optical body. The required coating of the body on the surfaces provided for reflection is not inexpensive. The optical body becomes useless if the coating is scratched during assembly or operation, and then it must be replaced. Another disadvantage of this inspection device is derived from the fact that the opposing reflective surfaces must be arranged at the same heights, thus requiring a relatively great distance between the imaging body and the side wall of the bottle mouth to be imaged. In addition, the side wall area of the mouth to be inspected can be detected only from an unfavorable angle, so the imaging quality is limited. Furthermore, all the light, even stray light, entering the optical imaging body is reflected. This device is also incapable of label inspection or the like, i.e., checking labels attached to the body of the bottle.

SUMMARY OF THE INVENTION

Consequently, the object of the present invention is to improve on an inspection device in this regard.

This object is achieved by the fact that the one-piece optical body made of a transparent material has a contour designed so that a full-range optical beam path coming from the lighted bottle to be imaged is deflected repeatedly by means of total reflection within the optical body on the path to the image recording element in its passage through the optical body. Because of the design of the body contour causing repeated total reflection of the optical beam, no opaque reflecting surfaces are necessary, so this reduces the manufacturing cost. According to one embodiment of the invention, the surfaces of the optical body causing the total reflection are arranged advantageously at offset heights to one another with at least triple total reflection so that the portions of a bottle to be inspected in the full circumference can be detected from a more advantageous angle. This embodiment is especially advantageous in inspection of a thread.

Since mirrorized surfaces are unnecessary, in contrast with the known related art, the peripheral areas of the bottle to be inspected are lighted from above through the optical body, with the advantage that problem-free ring lighting can be achieved, and secondly, undefined beams of light which are unwanted for the inspection are not reflected in the direction of the image recording element when the limiting angle which is definitive for the total reflection is exceeded, but instead such light can escape the optical body to the outside.

BRIEF DESCRIPTION OF THE DRAWINGS

Preferred embodiments are explained below on the basis of the figures, which show.

DESCRIPTION OF THE PREFERRED EMBODIMENT

Figure 1A:
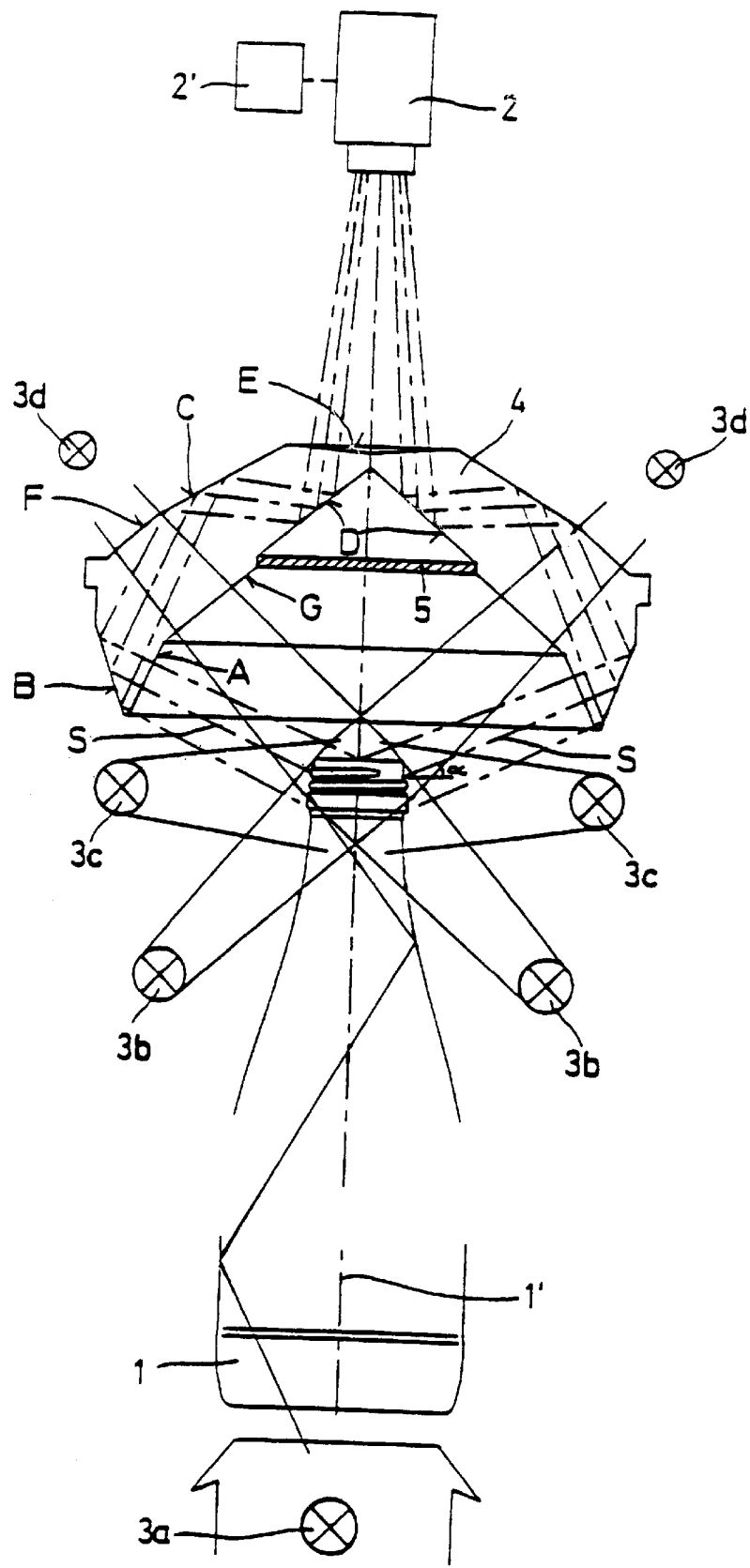
FIG. 1a is a vertical section through an optical body for the mouth side wall inspection of bottles, especially with a screw thread.

The rotationally symmetrical body 4 shown in FIG. 1a is arranged coaxially below a CCD camera 2 pointing down. The image is recorded at the moment when an empty bottle 1 to be inspected with its vertical axis 1' is briefly aligned essentially with the optical axis of the camera 2 and the axis of symmetry of body 4 during its continuous conveyance. The image is analyzed by using an electronic analyzer 2' by means of which the bottles imaged are then classified as "good" or "bad" accordingly.

The empty bottle 1 which is open at the top and is made of a transparent material is lighted by a light source 3a, which is arranged beneath the bottom of the bottle, or by a light source 3c positioned at the side next to the bottle wall section to be inspected. Furthermore, the corresponding bottle wall section can be lighted at an oblique angle from top to bottom or vice versa, from bottom to top through light sources 3c and 3d placed above or below the mouth of the bottle. Since optical body 4 does not have any mirrorized surfaces, the light source 3d needed for lighting from above may also be arranged above the optical body, and, since it is outside the linear bottle conveyance path there, it is ideally designed in a ring shape in the manner of a toroidal body. Thus, a uniform lighting can be achieved over the entire circumference, especially the mouth area for inspection of the sealing surfaces.

The different lighting variants mentioned above can be used not only as alternatives but also in suitable combinations, depending on the properties of the bottle (contour, etc.) and the areas to be inspected. If light cannot be shone through the bottles, light is directed in the incident lighting method is provided by light sources 3b through 3d, and then the bottom light source can be omitted.

The optical beam S shown in FIG. 1a is determined by the selected contour of optical body 4 which has three inclined sectional surfaces B, C, D such that an optical beam S coming from the mouth side wall of bottle 1, directed obliquely from bottom to top, entering body 4 made of glass or a plastic such as acrylic will be deflected a total of three times by total reflection on surfaces B, C, D, finally emerging from body 4 at the top and converging, then traveling on to camera 2. It is self-evident that the inclination of the three above-mentioned surfaces B, C, D with respect to the incident optical beam S is selected so that the angle does not drop below the limiting angle which depends on the material and is definitive for the total reflection. Especially useful images can be achieved when the angle of inclination of the middle axis of the optical beam section striking the mouth area is in a range of 15 to 30 degrees, based on the horizontal mouth area, especially 27 degrees.

Due to the fact that the first surface section B is arranged at a lower level than the second surface section C, which also lies on the outside surface, the lower edge of the rotationally symmetrical disk body 4, which is in the form of a hollow truncated cone, extends right up to the mouth of bottle 1 to be inspected, so it is possible to take a mostly side image of the mouth side wall area which has a screw thread, i.e., the optical beam 5, which diverges to the full extent from the mouth of the bottle, forms an acute angle with the horizontal. Owing to the inclination of the optical beam entry surface A, which is located in the lower area of body 4, and outside surface section B, the body 4 has a blade-shaped lower edge, as seen in cross section.

The inside surface labeled as A on the lower edge of the body is oriented at a right angle to the central axis of the optical beam S coming from the side wall of the mouth of the bottle, i.e., the plumb line of the entry surface A is aligned with the axis of the optical beam. This prevents refraction in the transition from the optically less dense medium to the optically denser medium. For the same reason, the outlet surface E which is on the top side of body 4 and faces camera 2 is also inclined so that it is passed perpendicularly upward in the direction of the camera by the emerging beam.

Furthermore, optical body 4 has two opposing, inclined, parallel surface sections G and F on its inside and outside contour; they are arranged with respect to the mouth of the bottle so that in the case of lighting of the mouth with a light source 3d arranged above body 4, a portion of the emitted light can pass through body 4 normal to surface sections G and F aligned in the direction of the mouth of the bottle, essentially without any refraction.

If a bottom light source 3a is used, but no bottom inspection of the bottle is necessary or is not to take place in conjunction with the inspection of the side wall of the mouth, an opaque disk 5 may be used in the hollow space of body 4 above the surface section G, so that the light coming vertically from the bottom of the bottle and passing upward through the inside cross section of the mouth will not reach the lens of the camera.

In this last point mentioned above, the variant of body 4 illustrated in FIG. 1b is different; in this variant, inspection of the inside wall, the bottom and the mouth sealing surface can take place simultaneously with inspection of the thread by means of bottom lighting, where recording of the image of the full extent of the mouth side wall takes way in the same manner as in the embodiment illustrated in FIG. 1a. In the variant according to FIG. 1b, there is no opaque disk at the center of the body, so that light bundle SZ coming out of the mouth of the bottle and the mouth sealing surface can pass vertically upward through body 4 to camera 2 unhindered. In contrast with the embodiment in FIG. 1a, body 4 according to FIG. 1b has two horizontal parallel surfaces H and I on the inside and outside of its upper central part through which the vertical beam of light SZ imaging the mouth and the bottom of the bottle can pass essentially without refraction. As shown in the figures, the surface sections A, B, C, D, F and G which have a circular curvature in the circumferential direction have straight surface lines.

Figure 1B:
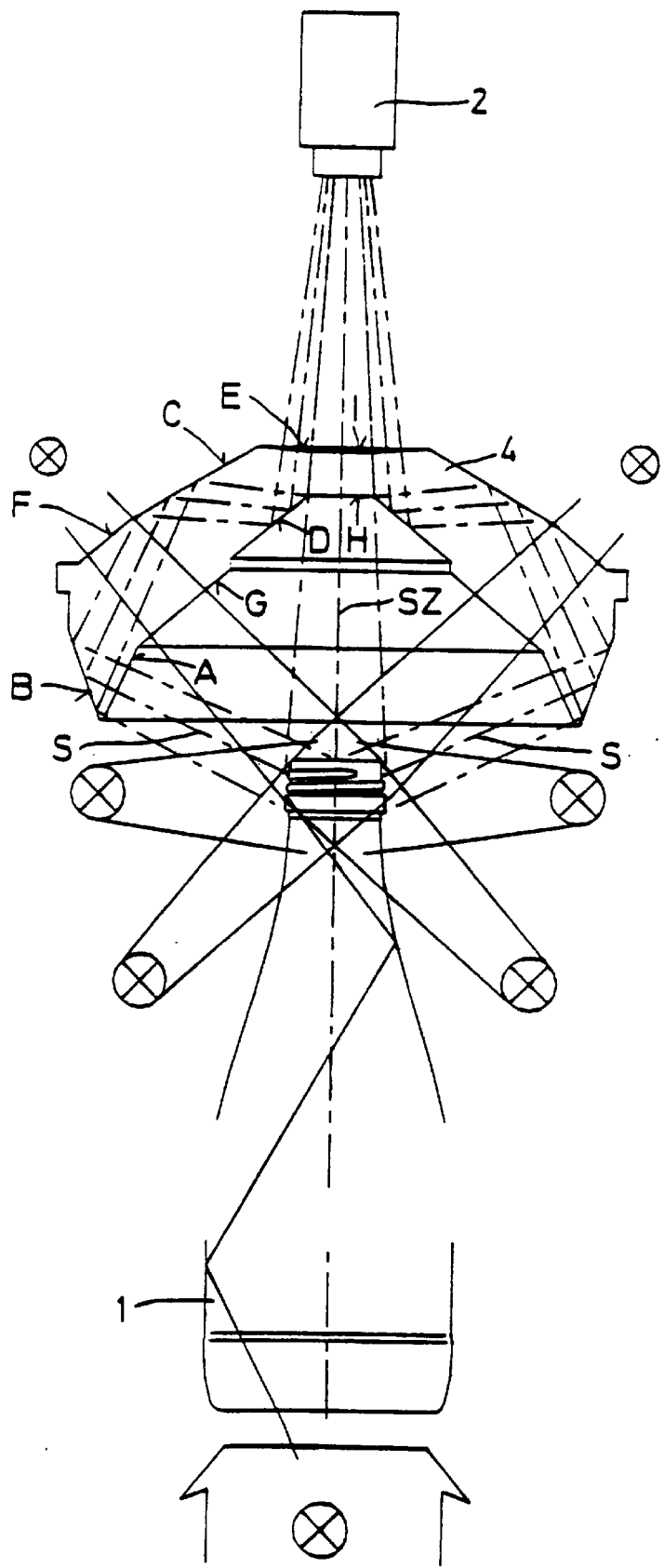
FIG. 1b is a second embodiment of an optical body with which it is also possible to inspect the inside wall, the bottom and the mouth sealing surfaces of transparent bottles.
Figure 1C:
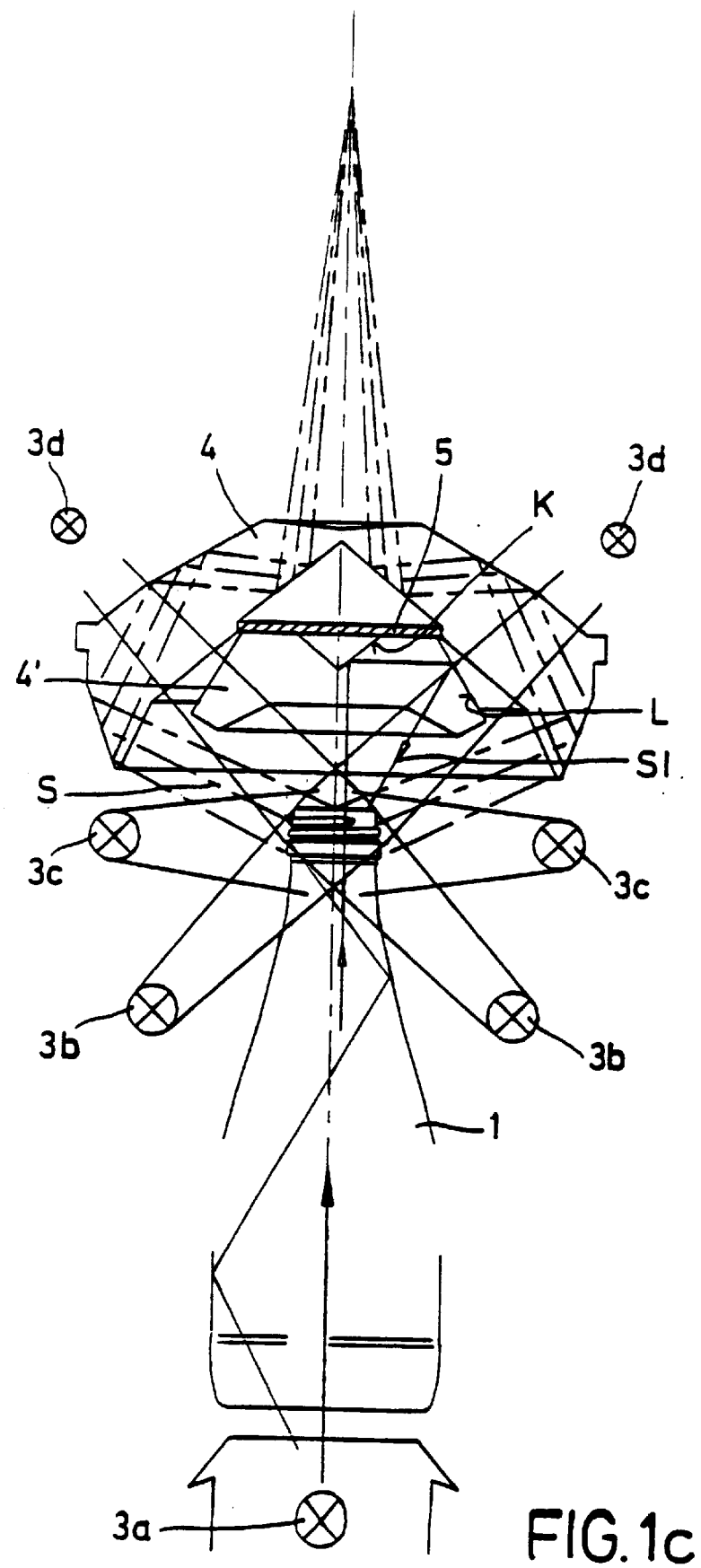
FIGS. 1c through 1e is an optical body corresponding to FIG. 1a with a second concentric optical body in three different embodiments.
Figure 1D:
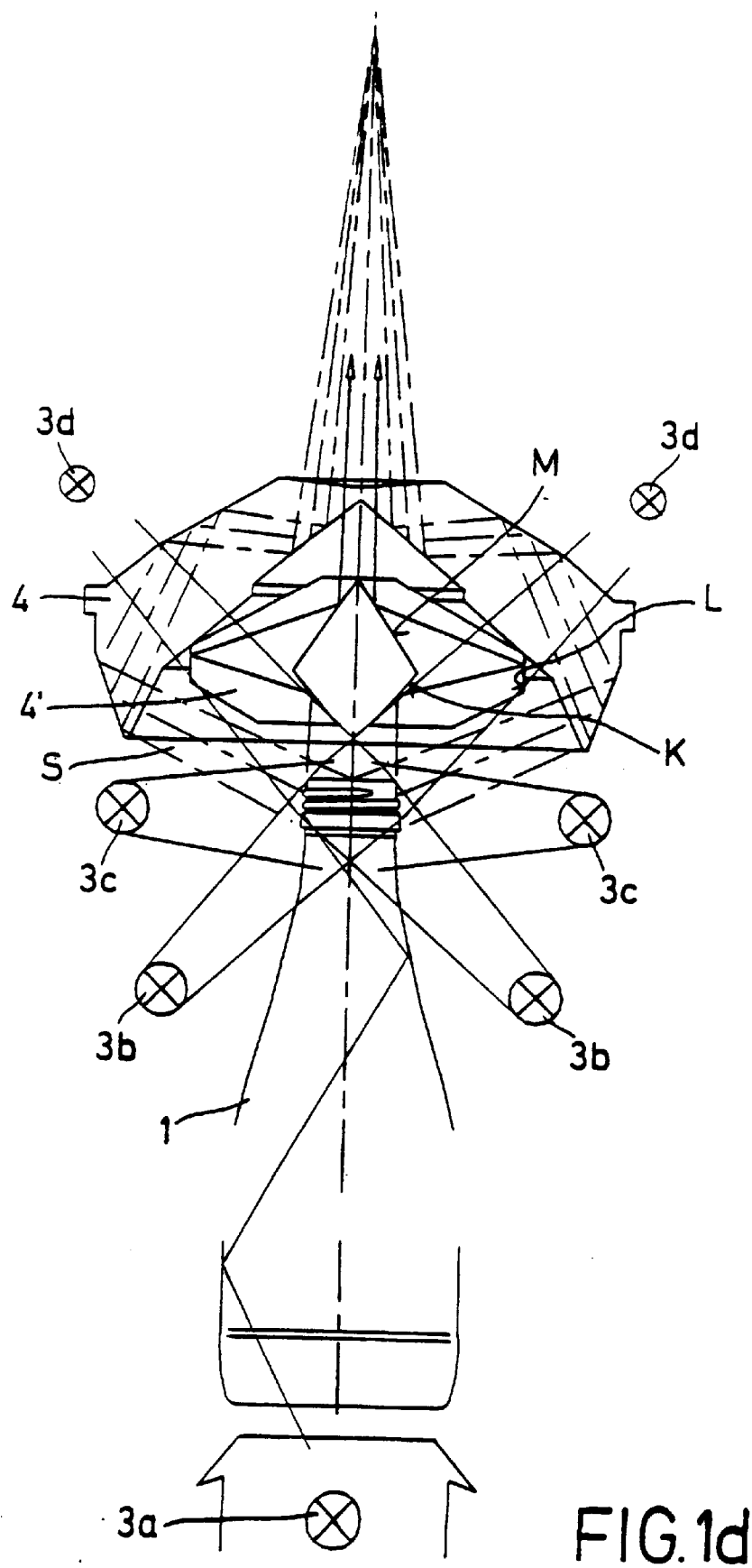

The variants shown in FIGS. 1c through 1d differ from the embodiments in FIGS. 1a and 1b in an additional body 4' attached concentrically in the interior of body 4, e.g., with adhesive. FIG. 1c shows light coming light source 3a upward out of the mouth of the bottle is reflected by body 4' which is also made of an opaque material by being reflected twice on two conical body surfaces K and L so that it strikes the mouth sealing surface obliquely from above and lights it optimally.

Figure 1E:
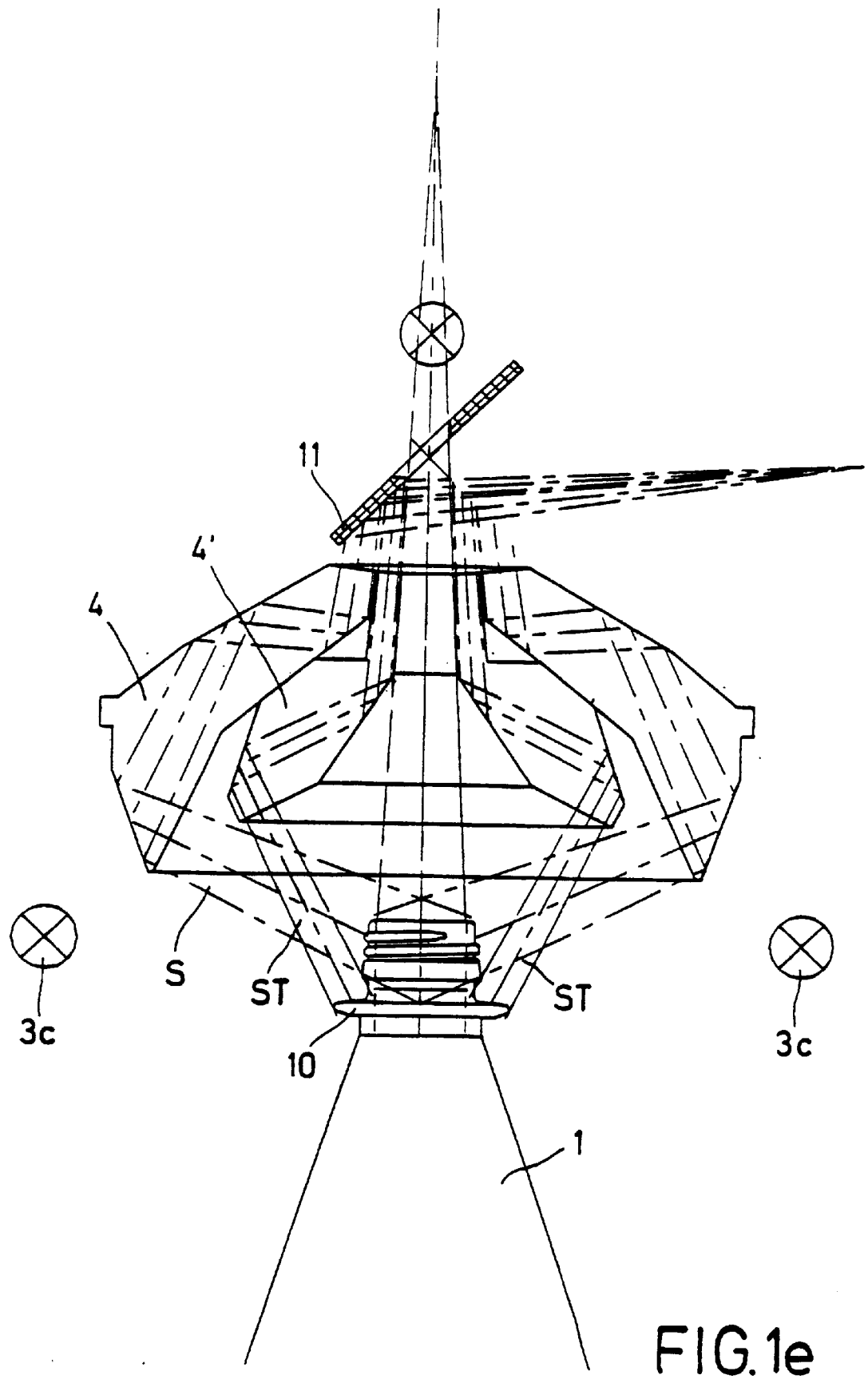

Body 4' in FIG. 1d is shaped so that light coming upward out of the mouth of the bottle and its sealing surface is reflected to the camera on three body surfaces K, L and M by total reflection in each case. FIG. 1e shows a body 4' which serves to inspect a supporting ring 10 in the area below the mouth. The full-range optical beam ST formed by total reflection twice has an optimal angle of incidence for detecting cracks, chips or codes on the supporting ring. The optical beams can be deflected toward a camera at the side by a ring wheel shaped mirror 11, so that the bottle can be lighted from above, through the hole in the middle of the mirror.

Figure 2A:
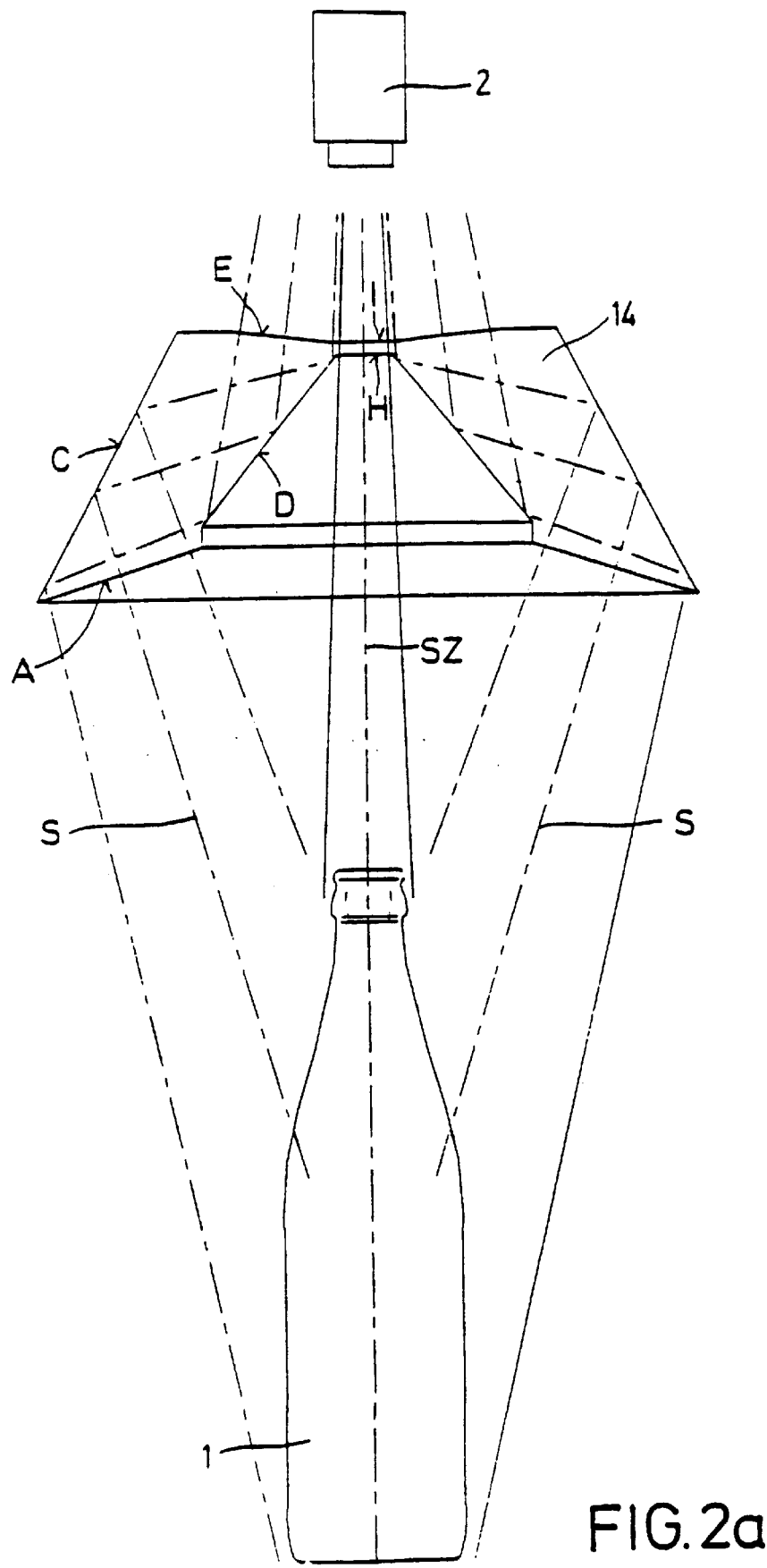
FIGS. 2a through 2d is a vertical section through an optical body for imaging the side wall of a bottle.

FIG. 2a shows an optical body 14 whose geometry and inside and outside contours are designed so that the side wall of the bottle is imaged completely over its entire height. At the same time, as in the embodiment according to FIG. 1b, the bottom of the bottle and the mouth sealing surface can be inspected for damage or soiling by using appropriate lighting. To this end, a centrally oriented optical beam SZ running vertically is directed through the center of body 14 to the camera 2. As in the embodiment according to FIG. 1b, the optical body has a horizontal section in the center with parallel surfaces H and I for the optical beam SZ coming from the mouth of the bottle, so that it images the sealing surface of the mouth and the bottom of the bottle in camera 2. Here again, there is essentially no refraction in the passage of the optical beam through the parallel surfaces H and I.

As in the embodiments described above, the beam inlet and outlet surfaces A and E with the optical body 14 illustrated in FIG. 2a are arranged so that an optical beam S encompassing the side wall of the bottle passes through these surfaces perpendicularly, i.e., essentially without refraction. In passage through optical body 14, optical beam S is reflected twice by total reflection on an outside surface of the body and on an inside surface of the body (unmirrorized), where a beam S running obliquely upward from the outside wall of the bottle, after entering the optical body 14, is then reflected first radially inward by the outside surface C to the second inside surface D, where it is again reflected upward to a CCD camera 2. The bottle can be lighted from the bottom and/or the side. The two surfaces C and D have a circular curvature in the circumferential direction, but they have straight side lines. With body 14, the entire outside wall of the bottle can be projected to the full extent onto camera 2, where it is imaged as a circle. The image is then analyzed in the traditional manner to detect damage or soiling.

As an alternative, there is the possibility of designing the optical body 14 in the form of a truncated pyramid, so that the surfaces causing the total reflection consist of several flat component surfaces offset in the circumference. With such a contour or geometry, it is possible to minimize the imaging errors caused by distortion, which cannot otherwise be avoided entirely with curved surfaces. This design can also be applied to the optical body 4 illustrated in FIGS 1a and 1b.

Figure 2B:
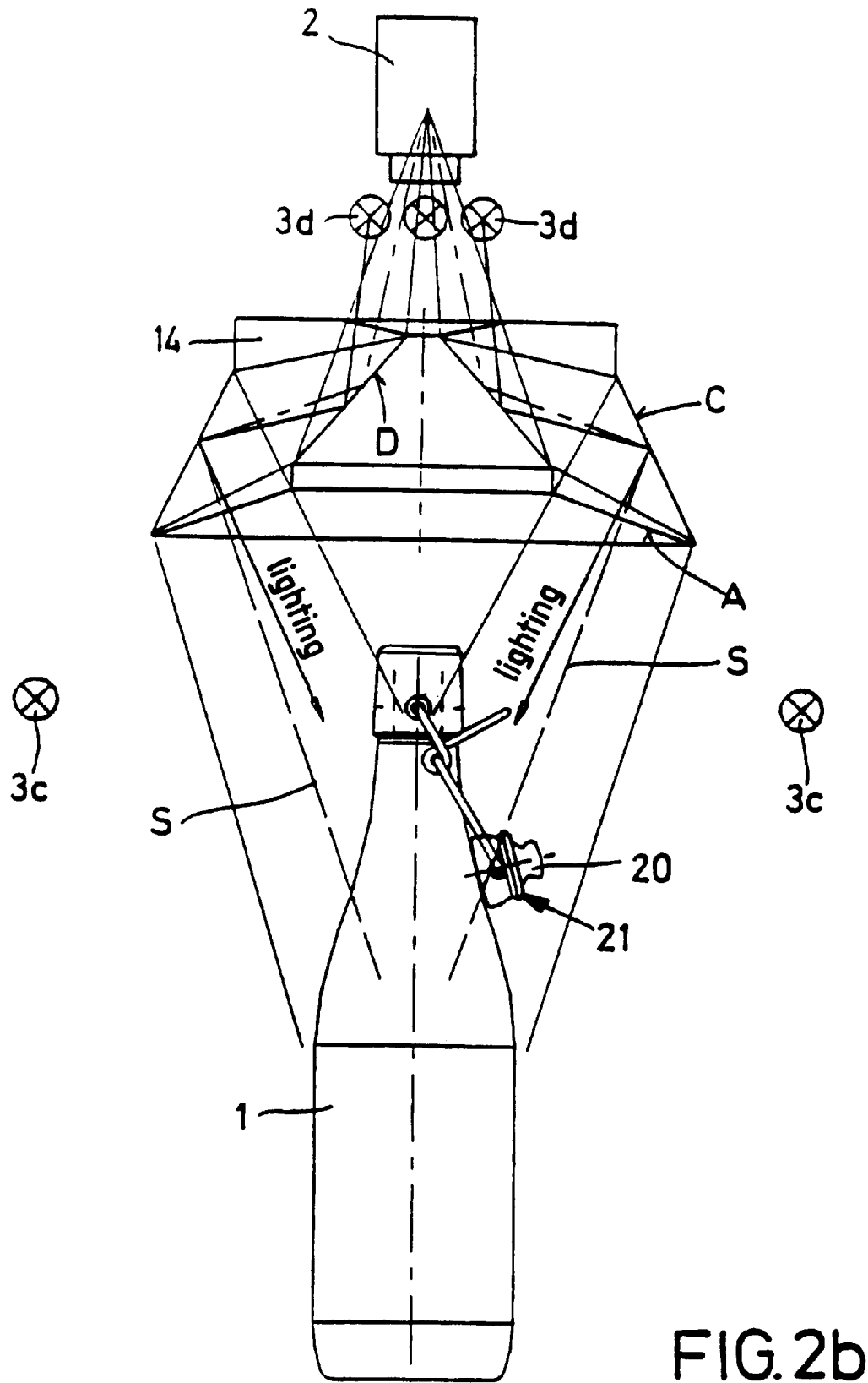

FIG. 2b shows an especially advantageous application of body 14, where certain quality features on the cylindrical surface of the bottle, which may be at any location on the circumference, can be detected in a controlled manner with the least effort on the basis of the full-extent imaging of the cylindrical surface of the bottle, without having to align the bottle before recording the image, as has been the case in the past, e.g., for inspecting the closure of a clip-lock bottle (see European Patent 512,539 B1). Body 14 projects the entire shoulder surface of an opened clip-lock bottle onto camera 2, whose image analyzing device then determines first the position of the bottle closure 20 from the circular image and then checks for the presence of a rubber sealing ring 21. As already explained in conjunction with FIGS. 1*a* and 1*b,* the lighting can be provided by suitable lighting elements 3*c,* 3*d* from the side or from above. The bottles to be inspected can easily be conveyed continuously in any rotational position beneath the body 14 by a plate conveyor or the like.

Figure 2C:
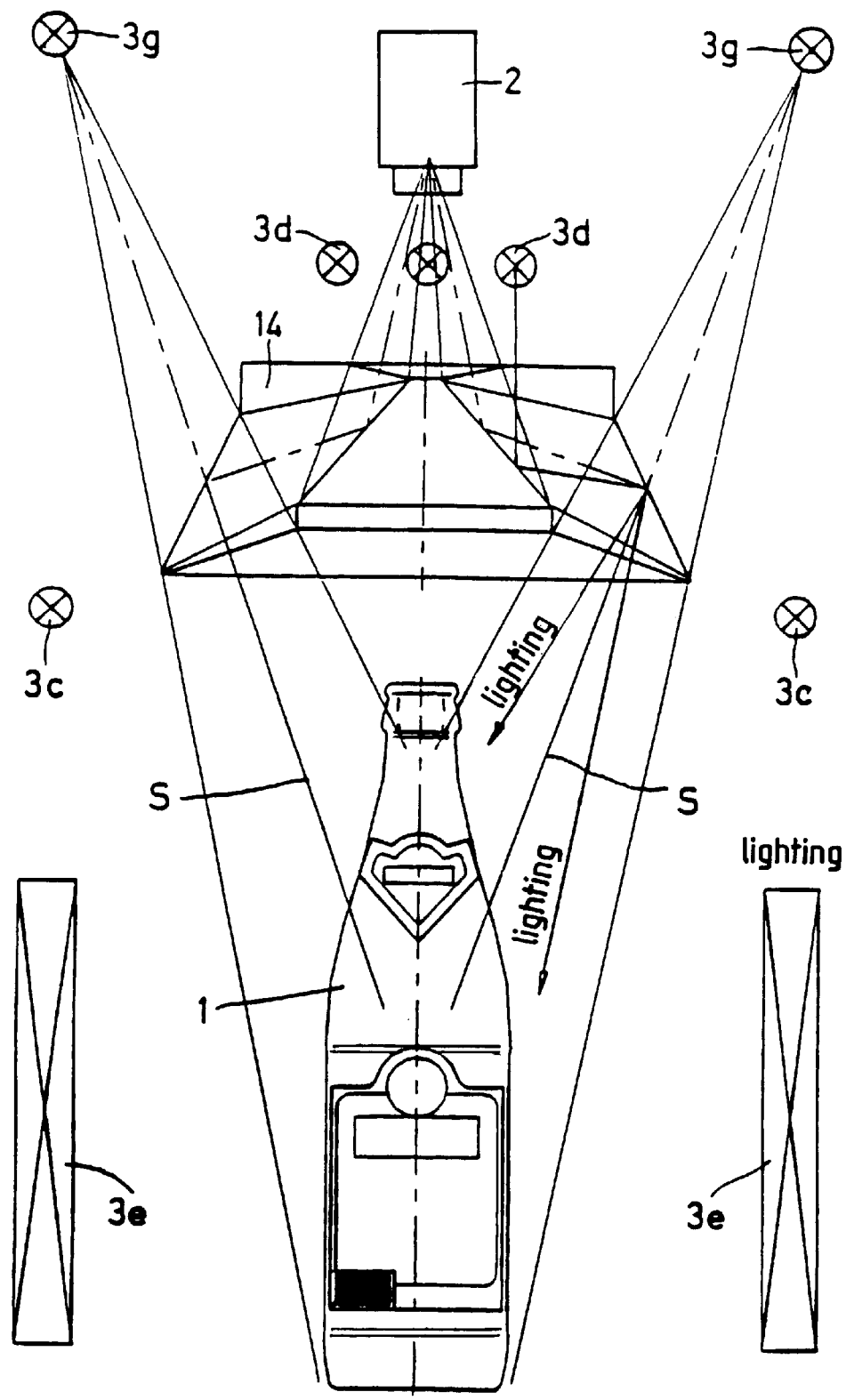

Labels can also be inspected in the same way to detect misaligned, missing or defective labels, i.e., those with an inverted logo or bar code (FIG. 2*c*). Here again, the entire lateral surface is recorded here first to the full extent to determine the position of the labels from the circular image. For this task, the correct position, shape and alignment of the labels with regard to the vertical axis of the bottle, the loco and the bar code of the labels can be given to the image analyzing device as preset values. The light can in turn be provided by lighting bodies 3*c,* 3*d,* 3*e,* 3*g* from the side or from above.

Figure 2D:
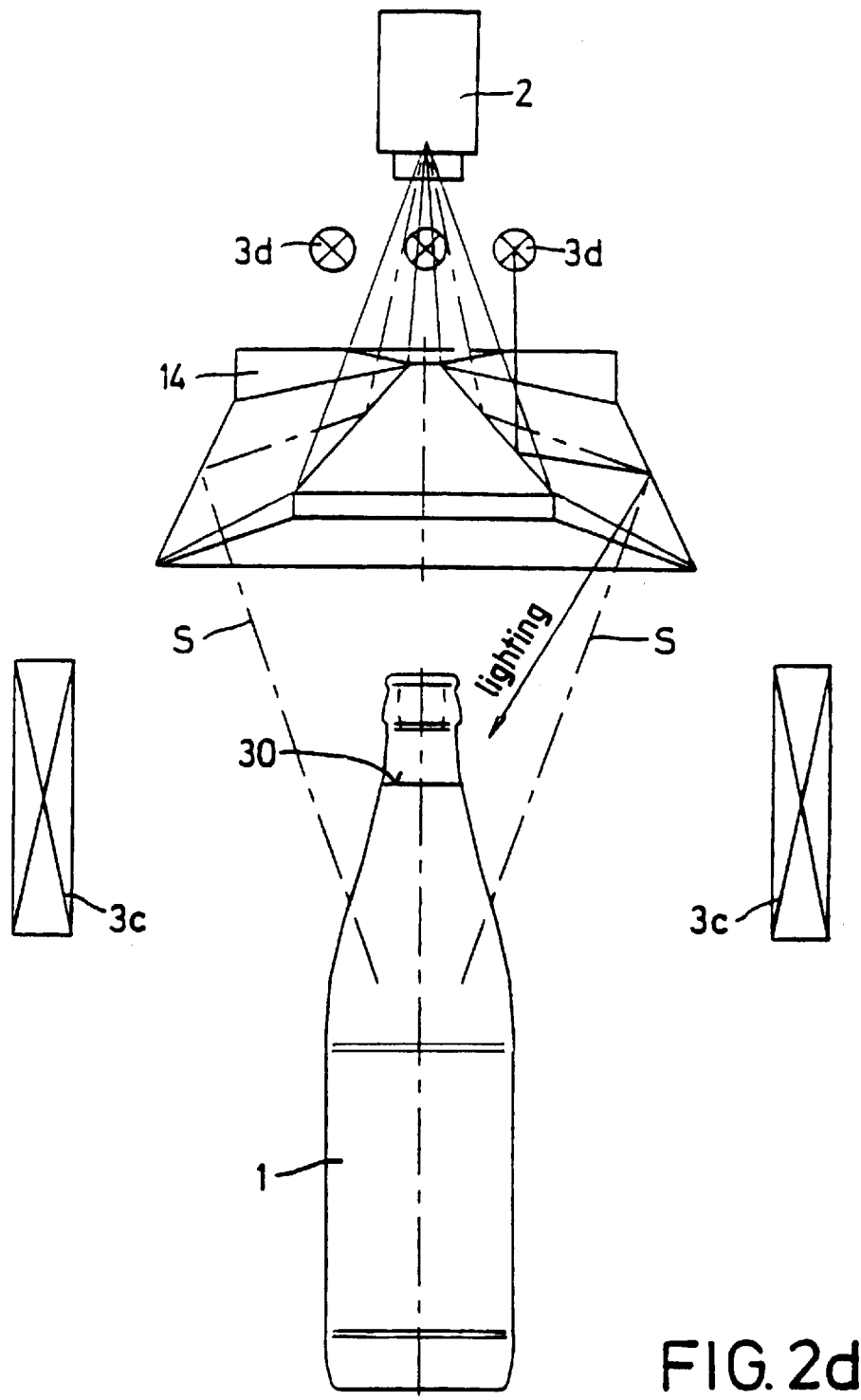
Figure 2D:
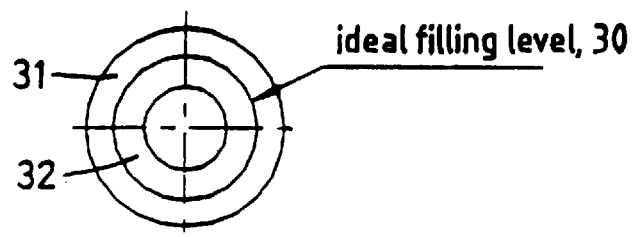

According to FIG. 2*d,* with the help of body 14, with a filled bottle made of a transparent material, it is also possible to inspect the filling level 30, which appears as a circular line between two circular rings 31, 32 with a difference in brightness in the figure. This filling level inspection is also possible to advantage even when there is a label in the area of the filling level, covering the bottle only partially, where the circumferential area without a label is used for image analysis.

I claim:

1. Device for inspecting bottles or the like, comprising in combination at least one light source (3) for lighting the bottles, an image recording element (2), an image analyzing device, and a one-piece optical body (4, 14) made of a transparent material whose contour is shaped so that there is at least one optical beam (S) which images a lighted bottle (1) to the full circumferential extent at least in various surface section areas, and wherein the light of said at least one optical beam is reflected several times by total reflection in its passage through said optical body (4, 14).

2. Device according to claim 1, wherein the inlet and outlet surfaces (A, E) of said optical body are aligned at right angles to the axis of the portion of said optical beam (S) coming from the area of the bottle to be imaged .

3. Device according to claim 1, wherein said optical body (4) that can be used in particular for inspection of the thread and the side wall of the mouth of the bottle has two outside surface sections (B, C) and one inside surface section (D), said respective outside and inside surface sections being so oriented at an angle to one another so that there is total reflection of said optical beam on these said sections.

4. Device according to claim 3, wherein said two outside surface sections (B, C) are offset at different heights one above the other and are inclined essentially in opposite directions.

5. Device according to claim 3, wherein said optical beam comes from the bottle (1) to be lighted so that its axis runs at an acute angle ($\alpha$) between 15° and 30° to the plane of the mouth or to the horizontal, wherein said optical beam first strikes said first outside surface section (B) which is at the lower end, is reflected there to said second outside surface section © which is at a higher level, and then is reflected by this to said inside surface section (D), which in turn causes total reflection toward said image recording element (2).

6. Device according to claim 5, wherein the inclination of said inside surface section (D) is selected so that the optical path imaging the bottle to the full extent, and at least in some areas converges toward said image recording element (2).

7. Device according to claim 3, wherein said optical body (4, 14) has a light incidence surface (A) facing toward the bottle (1) for said optical beam (S) coming from the bottle to be imaged, and said light incidence surface forms a blade-shaped lower edge on said optical body (4, 14) with said first outside surface section (B) which produces total reflection.

8. Device according to claim 1, wherein said optical body (4, 14) has a lower edge arranged above the mouth of the bottle.

9. Device according to claim 1, wherein said optical body (4, 14) is designed as a closed, essentially disk-shaped body with a hood-shaped vertical cross section.

10. Device according to claim 1, wherein said optical body (4, 14) has a hollow space which tapers from its bottom side in the direction of the top side, and its central area has a stop (5) to prevent axial passage of light from the mouth of the bottle to said image recording element (2) arranged above it, especially when the bottle (1) is lighted from the bottom of the bottle.

11. Device according to claim 1, wherein a light source (31) is positioned below the bottle (1) and lights the bottom of the bottle.

12. Device according to claim 1, wherein a light source (3*b*) is arranged at the side below the circumferential section of the bottle to be inspected, and lights the bottle from the outside obliquely upward in the direction of the mouth of the bottle.

13. Device according to claim 1, wherein a light source (3*c*) is arranged at the side next to the circumferential section of the bottle to be inspected and lights the bottle from the outside.

14. Device according to claim 1, wherein a light source (3*d*) is arranged above the mouth of the bottle and lights the circumferential section of the bottle to be inspected obliquely from above.

15. Device according to claim 14, wherein said light source (3*d*) is arranged above said optical body (4) and lights the circumferential section of the bottle to be inspected through said optical body (4).

16. Device according to claim 15, wherein inlet surface section (F) and the outlet surface section (G) for said light source (3*d*) on said optical body (4) are designed so that said beams of light coming from said light source (3*d*) pass through said surface sections (F, G) essentially at right angles.

17. Device according to claim 10, wherein a light source is arranged in said hollow space of said optical body (4).

18. Device according to claim 1, wherein said optical body (4, 14) is aligned so it is coaxial with the optical axis of said image recording element (2), and the image is recorded when the vertical axis of the bottle is aligned essentially with the optical axis of said image recording element (2).

19. Device according to claim 1, wherein said image recording element (2) is a CCD camera with a lens.

20. Device according to claim 1, wherein the contour of said optical body (4) is shaped so that the mouth side wall area of a bottle (1) is detected to the full extent, especially including a screw thread in this area.

21. Device according to 1, wherein the contour of the optical body (14) is shaped so that the side wall of the bottle is detected to the complete extent over its entire height.

22. Device according to claim 1, wherein said optical body (4, 14) has one of two parallel surfaces (H, I) or an opening in the center for inspection of one of the side wall, the bottom, or the mouth sealing surface.

23. Device according to, wherein optical body (4, 14) is designed with rotational symmetry.

24. Device according to claim 1 optical body has the shape of a truncated pyramid.

25. Device according to claim 3, wherein said surface sections (B, C, D) of said optical body (4, 14) responsible for the total reflection of an optical beam (S) have straight side lines.

26. Device according to claim 1, wherein said optical body is designed so that at least two said optical beams inclined at different angles to the vertical axis of the bottle are produced.

27. Device according to claim 26, wherein a first said optical beam is used for imaging a bottle and a second said optical beam is used to light the bottle.

28. Device according to claim 27, wherein the mouth of an open bottle is imaged by a said first optical beam, with the bottle being lighted at the bottom.

29. Device according to claim 26, wherein one of said at least two optical beam images are of the end face or a neck of a bottle, and one or more additional of said at least two optical beam images the cylindrical side surface of the same bottle to the full extent.

30. Device according to claim 1, wherein said optical body consists of multiple individual bodies arranged concentrically.

31. Device for inspecting bottles or the like, for checking by means of lighting at least one quality feature in the are of the cylindrical side surface of a bottle or the like, comprising in combination an image recording device, a respective image analyzing device, the cylindrical side surface of a bottle being detected to the full circumferential extent by means of at least one optical means which projects an optical beam coming from the cylindrical surface onto said image recording device, is imaged on said image recording device, and is processed by said image analyzing device.

32. Device according to claim 31, wherein said cylindrical side surface is detected to the full extent and imaged by said optical means over the entire height of said cylindrical surface.

33. Device according to claim 32, wherein said image analyzing device first determines the position of said at least one quality feature in any position on the height or circumference of said cylindrical side surface of the bottle from the complete image, and then compares said quality feature position with a predetermined setpoint or reference pattern and delivers a signal when there is an inadmissible deviation.

34. Device according to claim 31, wherein said at least one quality feature to be inspected is from the group consisting of the sealing surface of a clip-lock bottle closure, a label on said cylindrical side surface of a bottle, the label shape, the label position, the label color, a logo on the label, a bar code on the label and an imprint on the label.

35. Device according to claim 33, wherein said at least one quality feature to be inspected is the filling level of a bottle made of a transparent material.

36. Device according to claim 31, wherein said optical means are arranged in a stationary position above the bottles or the like that can be conveyed continuously by a conveyor device, and further wherein said optical means are an made of a transparent material.

37. Device according to claim 1, wherein the inlet and outlet surfaces (A, E) of said optical body are aligned at right angles to the axis of the section of said optical beam (S) leading to said image recording element (2).

38. Device according to claim 11, wherein said light source is a stroboscopic lamp.

39. Device according to claim 15, wherein said light source (3*d*) is designed as a ring.

40. Device according to claim 19, wherein said lens is a telocentric lens.

41. Device according to claim 24, wherein said shape of a truncated pyramid is the shape of a hollow truncated pyramid.

42. Device according to claim 29, wherein said one or more additional optical beams images the cylindrical side surface about the mouth side wall area of the bottle.

43. Device according to claim 29, wherein said one or more additional optical beams images the cylindrical side surface fully all at once.

* * * * *

UNITED STATES PATENT AND TRADEMARK OFFICE
CERTIFICATE OF CORRECTION

PATENT NO. : 6,072,575
DATED : June 6, 2000
INVENTOR(S) : Josef Loll

Page 1 of 1

It is certified that error appears in the above-identified patent and that said Letters Patent is hereby corrected as shown below:

<u>Column 5</u>
Line 59, "section © which is...." should be --(c) which is--;

<u>Column 7</u>
Line 26, "quality feature in the are" should be --quality feature in the area--.

Signed and Sealed this

Twelfth Day of June, 2001

*Attest:*

*Attesting Officer*

NICHOLAS P. GODICI
*Acting Director of the United States Patent and Trademark Office*